United States Patent [19]

Vecchietti et al.

[11] Patent Number: 4,994,450

[45] Date of Patent: Feb. 19, 1991

[54] AZACYCLIC COMPOUNDS AND THEIR USE AS ANALGESIC AGENTS

[75] Inventors: Vittorio Vecchietti, Milan; Antonio Giordani, Pavia, both of Italy

[73] Assignee: Dr. Lo. Zambeletti S.p.A., Italy

[21] Appl. No.: 309,687

[22] Filed: Feb. 10, 1989

[30] Foreign Application Priority Data

Feb. 12, 1988 [GB] United Kingdom ............... 8803259

[51] Int. Cl.⁵ .................. C07D 419/06; C07D 419/10; A61K 31/40; A61K 31/445
[52] U.S. Cl. ..................... 514/183; 514/210; 514/212; 514/222.2; 514/235.5; 514/316; 514/319; 514/422; 514/423; 540/362; 540/450; 540/480; 540/481; 540/596; 540/597; 540/598; 540/602; 540/607; 544/60; 544/130; 544/141; 546/189; 546/202; 546/206; 546/208; 548/518; 548/540
[58] Field of Search ............... 546/208, 245, 189, 206; 514/326, 330, 183, 210, 212, 222.2, 235.5, 316, 319, 422, 423; 540/362, 450, 480, 481, 596, 597, 598, 602, 607; 544/60, 130, 141; 548/518, 540

[56] References Cited

FOREIGN PATENT DOCUMENTS 052311 5/1982 European Pat. Off. .
147085 7/1985 European Pat. Off. .
0232612 8/1987 European Pat. Off. .
249349 12/1987 European Pat. Off. .

OTHER PUBLICATIONS

Chemical Abstracts, vol. 102, No. 21, May 27, 1985, Abstract No. 179248m.

*Primary Examiner*—Mukurd J. Shah
*Assistant Examiner*—Philip I. Datlow
*Attorney, Agent, or Firm*—Jacobs & Jacobs

[57] ABSTRACT

A compound, or a solvate or salt thereof, of formula (I)

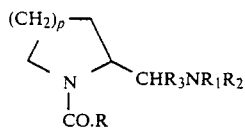

in which:

$R_1$ and $R_2$ are independently hydrogen, $C_{1-6}$ alkyl, $C_{2-6}$ alkenyl, $C_{3-6}$ cycloalkyl or $C_{4-12}$ cycloalkylalkyl groups, or together form a $C_{2-8}$ branched or linear polymethylene or $C_{2-6}$ alkenylene group optionally substituted with a hetero-atom, provided that $R_1$ and $R_2$ are not simultaneously hydrogen;

$R_3$ is hydrogen, $C_{1-6}$ alkyl, preferably methyl or ethyl, or phenyl, or $R_3$ together with $R_1$ form a $-(CH_2)_3-$ or $-(CH_2)_4-$ group;

p is 1, 2, 3 or 4, and

R is a group of formula (II)

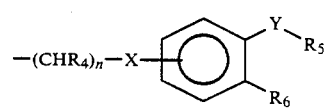

in which the group $-(CHR_4)_n-X-$ is in the meta- or para-position with respect to $YR_5$ or $R_6$, $R_4$ is hydrogen or $C_{1-6}$ alkyl, preferably hydrogen;

n is 0, 1 or 2, preferably 1;

X is a direct bond, or O, S or $NR_a$ in which $R_a$ is hydrogen or $C_{1-6}$ alkyl, and is preferably a direct bond;

Y is $>C=O$, $>CHOH$, $-S=O$ or $-SO_2$; each of $R_5$ and $R_6$ is $C_{1-6}$ alkyl, or $R_5$ and $R_6$ are linked together and $R_5$ represents $-(Z-)_m-$ where m is 0 or 1 and Z is O, S or $NR_7$ where $R_7$ is hydrogen or $C_{1-6}$ alkyl, and $R_6$ represents $-(CH_2)_q-$ where q is an integer of from 1 to 4, preferably 2 or 3, and in which one or more of the $-(CH_2)-$ groups is optionally substituted by a $C_{1-6}$ alkyl group, is useful for the treatment of pain.

19 Claims, No Drawings

AZACYCLIC COMPOUNDS AND THEIR USE AS ANALGESIC AGENTS

This invention is concerned with novel azacyclic derivatives, processes for their preparation, and their use in medicine, particularly as analgesics.

Compounds which are kappa-receptor agonists act as analgesics through interaction with kappa opioid receptors. The advantage of kappa-receptor agonists over the classical $\mu$-receptor agonists, such as morphine, lies in their ability to cause analgesia while being devoid of morphine-like behavioural effects and addiction liability.

European Published Application No. 232,612 discloses a group of azacyclic derivatives which exhibit kappa-receptor agonism without the behavioural effects of morphine and morphine analogues, and which are thus of potential therapeutic utility as analgesics.

A novel class of structurally related azacyclic derivatives has now been discovered which also exhibit potent kappa-receptor agonism without the aforementioned undesirable behavioural effects.

Furthermore, the novel class of derivatives show favourable binding affinity for spinal cord kappa-receptors, which potentially provides an opportunity to produce an analgesic effect without undesirable central effects.

According to the present invention there is provided a compound, or a solvate or salt thereof, of formula I:

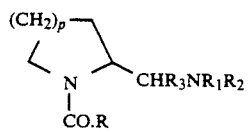

in which:
$R_1$ and $R_2$ are independently hydrogen, $C_{1-6}$ alkyl, $C_{2-6}$ alkenyl, $C_{3-6}$ cycloalkyl or $C_{4-12}$ cycloalkylalkyl groups, or together form a $C_{2-8}$ branched or linear polymethylene or $C_{2-6}$ alkenylene group optionally substituted with, provided that $R_1$ and $R_2$ are not simultaneously hydrogen;
$R_3$ is hydrogen, $C_{1-6}$ alkyl, preferably methyl or ethyl, or phenyl,
p is 1, 2, 3 or 4, and
R is a group of formula (II)

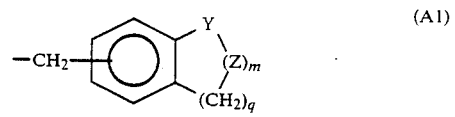

in which the group $-(CHR_4)_n-X-$ is in the meta— or paraposition with respect to $YR_5$ or $R_6$; $R_4$ is hydrogen or $C_{1-6}$ alkyl, preferably hydrogen;
n is 0, 1 or 2, preferably 1;
X is a direct bond, or O, S or $NR_a$ in which $R_a$ is hydrogen or $C_{1-6}$ alkyl, and is preferably a direct bond;
Y is $>C=O$, $>CHOH$, $-S=O$ or $-SO_2$;
each of $R_5$ and $R_6$ is $C_{1-6}$ alkyl, or
$R_5$ and $R_6$ are linked together and $R_5$ represents $-(Z-)_m-$
where m is 0 or 1 and Z is O,S or $NR_7$ where $R_7$ is hydrogen or $C_{1-6}$ alkyl,
and $R_6$ represents $-(CH_2)_q-$ where q is an integer of from 1 to 4, preferably 2 or 3, and in which one or more of the $-(CH_2)-$ groups is optionally substituted by a $C_{1-6}$ alkyl group.

The $C_{1-6}$ alkyl groups in the compounds of formula (I) may be straight or branched chains, and examples are methyl, ethyl, propyl, n-butyl, n-pentyl and n-hexyl, preferably methyl.

Examples of $C_{2-6}$ alkenyl groups are 1-and 2-propenyl; an example of a $C_{3-6}$ cycloalkyl group is cyclopropyl, and an example of a $C_{4-12}$ cycloalkylalkyl group is cyclopropyl methyl.

When $R_1$ and $R_2$ together form a linear or branched polymethylene group, examples are propylene, butylene, pentylene or hexylene, preferably butylene or 1-methylbutylene. As an alkenylene group $R_1-R_2$ may be typically $-CH_2-CH=CH-CH_2-$. Examples of hetero-atoms are oxygen and sulphur, particularly oxygen, and a suitable hetero atom substituted polymethylene group is $-CH_2CH_2OCH_2CH_2-$.

A preferred sub-group of formula (II) is a group of formula (A1)

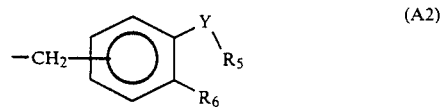

in which Y, Z, m, q and the position of $-CH_2-$ are as defined in formula (II), and one or more of the $-CH_2-$ groups in $-(CH_2)_q-$ is optionally substituted by $C_{1-6}$ alkyl.

Preferably, q is 2 when Z is oxygen and m is 1, and q is 2 or 3 when m is 0.

A further preferred sub-group of formula (II) is the group of formula (A2)

(A2)

in which Y is $C=O$ or CHOH, each of $R_5$ and $R_6$ is $C_{1-6}$ alkyl, preferably methyl, and the position of $-CH_2-$ is as defined in formula (II)

Particular examples of the group of formula (II) are:

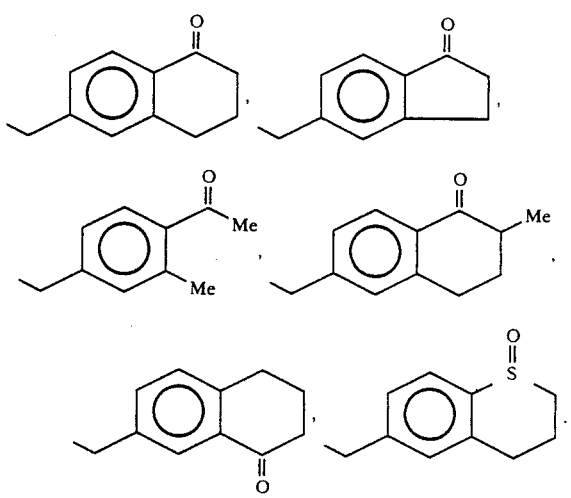

A particularly preferred group of compounds of formula (I) are those in which p=2, i.e. those based on a piperidine ring.

The compounds of formula I or their salts or solvates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula I or its salt or solvate.

One preferred pharmaceutically acceptable form is the crystalline form, including such form in a pharmaceutical composition. In the case of salts and solvates the additional ionic and solvent moieties must also be non-toxic.

Examples of a pharmaceutically acceptable salt of a compound of formula I include the acid addition salts with the conventional pharmaceutical acids, for example, maleic, hydrochloric, hydrobromic, phosphoric, acetic, fumaric, salicylic, citric, lactic, mandelic, tartaric, succinic, benzoic, ascorbic and methanesulphonic.

Examples of a pharmaceutically acceptable solvate of a compound of formula I include the hydrate.

The compounds of formula I have at least one asymmetric centre and therefore exist in more than one stereoisomeric form. The invention extends to all such forms and to mixtures thereof, including racemates. Examples of compounds of the invention are:

1-[1-oxo-3,4,-dihydro-(2H)-naphth-6-yl]acetyl-2-(pyrrolidin-1-yl)methyl-piperidine;
(2S)-1-[1-oxo-3,4,-dihydro-(2H)-naphth-6-yl]acetyl-2-(pyrrolidin-1-yl) methyl-piperidine;
(2S)-1-[1-oxo-2,3,-dihydroinden-5-yl]acetyl-2-(pyrrolidin-1-yl)methyl-piperidine;
(2S)-1-(3-methyl-4-acetylphenyl)acetyl-2-(pyrrolidin-1-yl)methyl-piperidine;
(2S)-1-[1-oxo-2-methyl-3,4-dihydro-(2H)-naphth-6-yl]acetyl-2-(pyrrolidin-1-yl)methyl-piperidine;
(2S)-1-[1-oxo-3,4-dihydro-(2H)-naphth-7-yl] acetyl-2-(pyrrolidin-1-yl)methyl piperidine; and
(2S)-1-[1-oxo-3,4-dihydro-(2H)-1-benzothiin6-yl)acetyl-2-(pyrrolidin-1-yl)methyl piperidine.

The present invention also provides a process for the preparation of a compound of formula I which comprises reacting a compound of formula (III)

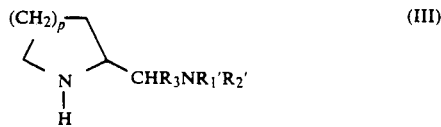
(III)

in which $R_3$ and p are as defined for formula (I), and $R_1$ and $R_2$ are $R_1$ and $R_2$ as defined for formula (I) or a group or atom convertible to $R_2$ and $R_2$, with a compound of formula

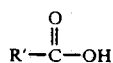

or an active derivative thereof, in which R' is R as defined for formula (I), or a group convertible to R, to form a compound of formula (Ia)

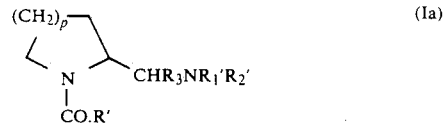
(Ia)

and then optionally performing one or more of the following steps:

(a) when R', $R_1'$, or $R_2'$ are other than R, $R_1$ and $R_2$, converting R', $R_1'$, or $R_2'$ to R, $R_1$ or $R_2$ to obtain a compound of formula (I), (b) where R', $R_1'$ and $R_2'$ are R, $R_1$ and $R_2$, converting one R, $R_1$, or $R_2$ to another R, $R_1$, or $R_2$ to obtain a compound of formula (I), (c) forming a salt and/or solvate of the obtained compound of formula (I).

Suitable active derivatives of

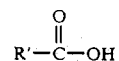

are acid chlorides or acid anhydrides. Another suitable derivative is a mixed anhydride formed between the acid and an alkyl chloroformate.

For example, in standard methods well known to those skilled in the art, the compound of formula (III) may be coupled:

(a) with an acid chloride in the presence of an inorganic or organic base, (b) with the acid in the presence of dicyclohexyl carbodiimide, N-dimethylaminopropyl-N'-ethyl carbodiimide or carbonyl diimidazole, (c) with a mixed anhydride generated in situ from the acid and an alkyl (for example ethyl)chloroformate.

It will be appreciated that a compound of formula (Ia) may be converted to a compound of formula (I), or one compound of formula (I) may be converted to another compound of formula (I), by interconversion of suitable substituents. Thus certain compounds of formula (I) and (Ia) are useful intermediates in forming other compounds of the present invention.

$R_1'$ and $R_2'$ may be alkyl groups and converted to $R_1'/R_2'$ hydrogen atoms by conventional amine dealkylation. When $R_1'$ or $R_2'$ is benzyl or substituted benzyl it may be converted to an $R_1$ or $R_2$ hydrogen atom by catalytic hydrogenation or other method of reduction. $R_1'$ and $R_2'$ as hydrogen atoms may be converted to $R_1$ and $R_2$ alkyl groups by conventional amine alkylation, or by acylation followed by reduction. $R_1'$ and $R_2'$ are preferably $R_1$ and $R_2$ respectively.

The above described process will generally provide a diastereoisomeric mixture which can subsequently separated into isomers by column chromatography.

The compound

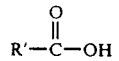

is typically of the formula (IIa)

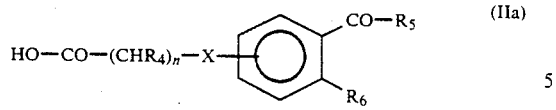

in which $R_4$, $R_5$, $R_6$, X and n are as defined for formula (II),

The reaction between compounds of formulae (III) and (IIa) will yield compounds of formula (I) in which Y is $>C=O$. Compounds of formula (I) in which Y is $>CHOH$ may be prepared by reducing the compounds in which Y is $>C=O$, preferably using mixed hydrides such as $NaBH_4$, $LiAlH_4$ or DIBAH.

The compounds of formula (I) may be converted into their pharmaceutically acceptable acid addition salts by reaction with the appropriate organic or mineral acids.

Solvates of the compounds of formula (I) may be formed by crystallization or recrystallization from the appropriate solvent. For example hydrates may be formed by crystallization or recrystallization from aqueous solutions, or solutions in organic solvents containing water.

Also salts or solvates of the compounds of formula (I) which are not pharmaceutically acceptable may be useful as intermediates in the production of pharmaceutically acceptable salts or solvates. Accordingly such salts or solvates also form part of this invention.

As mentioned before, the compounds of formula (I) exist in more than one stereoisomeric form and the processes of the invention produce mixtures thereof. The individual isomers may be separated one from another by resolution using an optically active acid such as tartaric acid. Alternatively, an asymmetric synthesis would offer a route to the individual form.

Compounds of formula (III) in which $R_3$ is hydrogen may be prepared from compounds of formula (Iv) by the following reaction scheme:

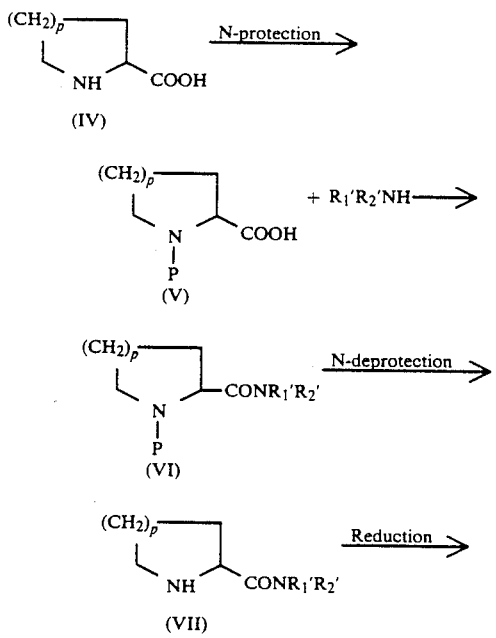

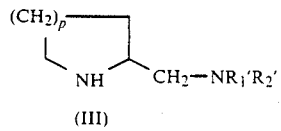

In this scheme, firstly the compound of formula (IV) is nitrogen protected with a conventional protecting group P, such as benzyloxycarbonyl or tert-butyloxycarbonyl, forming the compound of formula (V) which is reacted with the amine $R_1'R_2'NH$ (in which $R_1'$ and $R_2'$ are as defined earlier) to obtain an N-protected amide (VI). This is conventionally N-deprotected, for example by catalytic debenzylation if P is benzyloxycarbonyl or by acid treatment if P is tert-butyloxycarbonyl, and the resulting basic amide (VII) is reduced to the diamine (III) by reaction with lithium aluminum hydride.

Alternatively, the N-protected acid (V) is reduced to a primary alcohol which is esterified, for example with methane sulfonic acid or p-toluenesulfonic acid, and the ester reacted with $R_1'R_2'NH$. Deprotection of the ring nitrogen gives the diamine (III).

When the starting material of formula (IV) is a racemic mixture, the resulting compounds of formulae (III) and (I) are also racemic. Using a compound of formula (Iv) in the R- or S-configuration results in the corresponding optically active products.

Compounds of formula (III) in which $R_3$ is other than hydrogen and p is 2 may be prepared from a compound of formula (VIII) by the following reaction scheme:

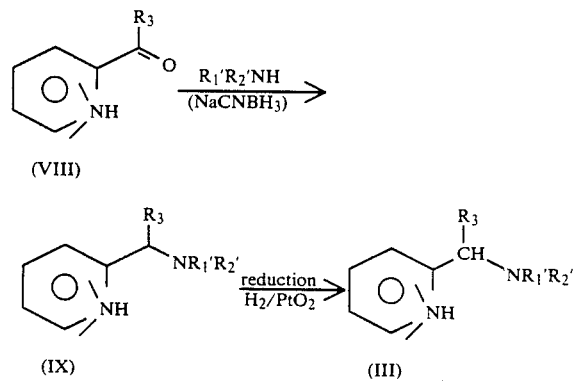

In this scheme a compound of formula (VIII) is treated with a secondary amine $R_1'R_2'NH$ (in which $R_1'$ and $R_2'$ are as defined earlier) in the presence of a reducing hydride, such as $NaCNBH_3$, to form a compound of formula (IX). The latter is then reduced catalytically using hydrogen/$PtO_2$ to form a compound of formula (III).

The intermediate compounds of formula (III) are novel, and as such form a further aspect of the present invention.

The compounds of formula (IV) are known compounds. When p=1, the compound is R—, S— or R,S— proline. When p=2 it is R—, S—, or R,S— pipecolinic acid (Beilstein 22/IV, 96-97), and when p=3 is it R—, S—, or R,S-hexahydroazepine —2— carboxylic acid (J. Med. Chem, 14, 501/1971).

The compounds of formula (VIII) are either known compounds or can be made from known compounds by known methods.

The compounds of formula (IX) in which $R_3$ and $R_1'$ together form a —$(CH_2)_3$— or —$(CH_2)_4$— group are known [L.C. Craig, J. Am. Chem. Soc. 56, 1144 (1934); Ramon Weil et al., Bull. Soc. Chim. France, 1974, 258] and these may be reduced to the corresponding compounds of formula (III) by known methods (Zh. Org. Khim. 1971, 7, (10), 2198–2201).

The compounds of formula

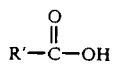

$$R'-C(=O)-OH$$

are also known compounds or can be prepared from known compounds by known methods (for example see J.O.C. 27 (1960), 70–76; Chem. Lett. (1981), 367–370).

The activity of the compounds of formula (I) in standard analgesic tests indicates that they are of therapeutic utility in the treatment of pain.

Accordingly the present invention also provides a compound of formula (I), or a pharmaceutically acceptable salt or solvate thereof, for use as an active therapeutic substance, particularly for use in treating pain.

The present invention further provides a pharmaceutical composition comprising a compound of formula (I), or a pharmaceutically acceptable salt or solvate thereof, and a pharmaceutically acceptable carrier.

The present invention also provides the use of a compound of formula (I), or a pharmaceutically acceptable salt or solvate thereof, in the manufacture of a medicament for the treatment of pain.

Such a medicament, and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known analgesic agents.

Preferably, a pharmaceutical composition of the invention is in unit dosage form and in a form adapted for use in the medical or veterinarial fields. For example, such preparations may be in a pack form accompanied by written or printed instructions for use as an agent in the treatment of pain.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi-dose forms such as a bottle from which the appropriate dose may be withdrawn or a solid form or concentrate which can be used to prepare an injectable formulation.

As mentioned earlier, the effective dose of compound depends on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

Within the above indicated dosage range, no adverse toxicological effects have been observed with compounds of the invention. The present invention also provides a method of treating pain in mammals, particularly in humans, which comprises administering an effective amount of a compound of formula (I), or pharmaceutically acceptable salt or solvate thereof, to a sufferer.

Compounds of this invention and their preparation are illustrated in the following Examples. The Descriptions illustrate the preparation of intermediate compounds.

DESCRIPTION 1

1-oxo-3,4,-dihydro-(2H)-naphth-6-yl acetic acid

A solution of 4.8 ml (32 mmoles) of diethyl malonate in 25 ml of dry dioxane was added dropwise to a stirred suspension of 1 g of sodium hydride, at 0° C. and under nitrogen atmosphere. 10 g (54 mmoles) of CuI were added and the suspension obtained was stirred for an additional half hour at room temperature; then 5 g (22 mmoles) of 6-bromo-1-tetralone (obtained as described by Allinger and Jones, JOC 27 70, 1962) dissolved in 25 ml of dry dioxane were added dropwise. The mixture was stirred under nitrogen at reflux for 6 hours, cooled, filtered, diluted with 250 ml of ethyl acetate and washed with two 10 ml portions of 5% hydrochloric acid, dried and evaporated in vacuo.

The oily material so obtained was separated by silica gel column chromatography. By elution with hexane/ethyl ether 1:1, 1.3 g (19%) of a yellow oil, which was characterized as 1,2,3,4-tetrahydro-1-oxo6-naphthyl-diethyl malonate, were obtained.

IR (neat) : $cm^{-1}$ 1755; 1740; 1650; 1590; 1275; 1035
NMR ($CDCl_3$): δ 1.3 (6H, t); 2.2 (2H, m); 2.6 (2H, t); 2.9 (2H, t); 4.2 (4H, q); 4.7 (1H, s); 7.4 (2H, m); 8 (1H, d).

This compound was dissolved in 8 ml of dioxane and added to 50 ml of 50% sulphuric acid. The solution obtained was heated at 60° C. for 8 hours, then cooled and diluted with 30 ml of water and extracted with ether, dried and evaporated in vacuo.

The dark oil so obtained was treated with hot cyclohexane and 0.8 g of the title product were obtained on standing.

MP: 106°–108° C.
IR (KBr): $cm^{-1}$ 1740; 1660; 1605; 1250; 1150
NMR ($CDCl_3$): δ 2.2 (2H, q); 2.7 (2H, t); 3 (2H, t); 3.7 (2H, s); 7.2 (2H, d); 8.0 (1H, d); 10.1 (1H, broad).

EXAMPLE 1

1-[1-oxo-3,4,-dihydro-(2H)-naphth-6-yl]acetyl-2-(pyrrolidin-1-yl)methyl-piperidine hydrochloride A solution of 0.8 g (3.9 mmoles) of 1-oxo-3,4,-dihydro-(2H)-naphth-6-yl acetic acid in 40 ml of dry chloroform was cooled to 0° C. and 0.68 ml (7.8 mmoles) of oxalyl chloride were added dropwise. After 24 hours the solution was evaporated in vacuo. the oily material so obtained was dissolved in 50 ml of dry chloroform, cooled to 0° C. and 0.65 g (3.9 mmoles) of 2-(pyrrolidin-1-yl)methyl piperidine dissolved in 5 ml of dry chloroform added dropwise. The mixture was stirred at room temperature for 3 hours and then 10 ml of methanol were added. The solution was evaporated in vacuo and the title compound (0.6 g, 40%), crystallized by treatment with ethyl acetate.

MW=390.941
MP=204–205° C.

| Anal. calcd. for $C_{22}H_{31}N_2O_2Cl$: | C | 67.58 found | 66.89 |
|---|---|---|---|
| | H | 7.99 | 8.02 |
| | N | 7.17 | 7.01 |
| | Cl | 9.06 | 8.93 |

IR (KBr): $cm^{-1}$ 1680; 1635; 1610; 1450; 1130
NMR ($CDCl_3$): δ 6 1.7 (6H, m); 2 (6H, m); 2.5 (2H, t); 2.9 (5H, m); 3.1–4.3 (5H, m);
3.9 (2H, d); 5.3 (1H dd); 7.2 (2H,m);
7.9 (1H, d); 11.7 (1H, broad).

EXAMPLE 2

(2S)-1-[1-oxo-3,4,-dihydro-(2H)-naphth-6-yl]acetyl-2-(pyrrolidin-1-yl)methyl-piperidine hydrochloride Analogously to the procedure described in Example 1, starting from (2S)-2-(pyrrolidin-1-yl)methylpiperidine, the title compound was obtained and crystallized from acetone (57.3% yield).
MW=390.941
MP=179°–180° C.
$[\alpha]_D = -49.2°$ C.=1 MeOH

EXAMPLE 3

(2S)-1-[1-oxo-2,3,-dihydroinden-5-yl]acetyl-2-(pyrrolidin-1-yl)methyl-piperidine A solution of 0.4g (2mmoles) of 1-oxo-2,3,-dihydroinden -5-yl acetic acid [obtained from the oxidation of 2,3-dihydro-(1H)-inden-5-yl acetic acid, prepared as described in J. Am Chem. Soc. 71, 1911 (1949)]in 20ml of dry chloroform was cooled to 0° C. and 0.35ml (4mmoles) of oxalyl chloride were added dropwise. After 24 hours the solution was evaporated in vacuo. The oily material so obtained was dissolved in 25ml of dry chloroform, cooled to 0°–5° C. and 0.4g (2.4mmoles) of (2S)-2-(pyrrolidin-1-yl)methyl-piperidine dissolved in 2ml of dry chloroform were added dropwise. The mixture was left at room temperature for 2 days, washed with a 32% $NH_4OH$ solution, the organic layer separated, dried over $Na_2SO_4$ and evaporated in vacuo to dryness. The crude product was purified by column chromatography, eluting with a mixture of $CH_2Cl_2$ and MeOH (0.5–2.5%), to yield 0.4 g of the title compound.
$C_{21}H_{28}N_2O_2$
M.W.=340.464

EXAMPLE 4

(2S)-1-(3-methyl-4-acetylphenyl)acetyl-2-(pyrrolidin-1-yl)methyl-piperidine hydrochloride hydrate A solution of 1g (5.2mmoles) of 3-methyl-4-acetylphenyl-acetic acid in 20ml of dry chloroform was cooled to 0° C. and 0.94ml (11mmoles) of oxalyl chloride were added dropwise. After 24 hours the solution was evaporated in vacuo, the oily material so obtained was dissolved in 30ml of dry chloroform, and added dropwise, under vigorous stirring, at 0° C. to a solution of 0.85g (5.1mmoles) of (2S)-2-(pyrrolidin-1-yl) methyl piperidine in 20ml of dry chloroform containing 0.8g of powdered $K_2CO_3$. The mixture was stirred at 0° C. for 2 hours and left overnight. The solution filtered and concentrated in vacuo to dryness. The crude product was chromatographed on silica gel eluting with a $CH_2Cl_2$MeOH mixture (0.5 to 2.5%) to afford a product which was treated with a HCl saturated Et₂O solution, and crystallized from ethyl acetate/acetone, to yield 0.8g of the title compound.

$C_{21}H_{30}N_2O_2 \cdot HCl \cdot H_2O$
M.W. = 396.947

Elemental analysis: Calcd. C, 63.54; H, 8.38; N, 7.05, Found C, 63.38, H, 8.35; N, 7.00.

$[\alpha]^{20}D = -57.6°$ (C=1 EtOH)

EXAMPLE 5

(2S)-1-[1-oxo-2-methyl-3,4-dihydro-(2H)-naphth-6-yl]acetyl-2-(pyrrolidin-1-yl)methyl-piperidine A solution of 0.4g (1.8mmoles) of 1-oxo-2-methyl-3,4-dihydro-(2H)-naphth-6-yl acetic acid [prepared from 1-oxo-3,4-dihydro-(2H)-naphth-6-yl acetic acid by bromination followed by methylation with MeI in the presence of Zn as described in J. Am. Chem, Soc. 89. 5727 (1967)] in 20ml of dry chloroform was cooled to 0° C. and 0.35ml (4mmoles) of oxalyl chloride were added dropwise.

After 24 hours the solution was evaporated in vacuo. the oily residue obtained was dissolved in 25ml of dry chloroform, cooled to 0° C. and 0.4g (2.4mmoles) of (2S)-2-(pyrrolidin-1-yl)methyl-piperidine, dissolved in 2ml of dry chloroform, were added dropwise. The mixture was left at room temperature for 2 days, washed with a 32% NH₄OH solution, the organic layer separated, dried over Na₂SO₄ and evaporated in vacuo to dryness. The crude product obtained was purified by column chromatography eluting with a mixture of CH₂Cl₂ and MeOH (0.5 to 2.5%), to yield 0.5g of the title compound.

$C_{23}H_{32}N_2O_2$
M.W. = 368.518

EXAMPLE 6

(2S)-1-[1-oxo-3,4-dihydro-(2H)-naphth-7-yl]acetyl-2-(pyrrolidin-1-yl)methyl-piperidine hydrochloride A solution of 1g (4.9mmoles) of 1-oxo-3,4-dihydro(2H)-naphth-7-yl acetic acid (see GB-A-2030140) in 30ml of dry chloroform was cooled to 0° C. and 0.72ml (8.2mmoles) of oxalyl chloride were added dropwise.

After 24 hours the solution was evaporated in vacuo, the crude material so obtained was dissolved in 10ml of dry chloroform, cooled to −5° C. and 1.4g of K₂CO₃ were added. To the suspension 0.83g (4.9mmoles) of (2S)-2-(pyrrolidin-1-yl) methyl piperidine, dissolved in 30ml of dry chloroform, were added dropwise under vigorous stirring and left overnight. The suspension was washed with 20ml of H₂O for 30 minutes diluted with CH₂Cl₂ and the organic layer separated, dried over Na₂SO₄ and concentrated in vacuo to dryness. The crude product obtained was purified by column chromatography eluting with a mixture of CH₂Cl₂ and MeOH (0.5 to 2.5%), to afford a product which was treated with an HCl saturated Et₂O solution, and crystallised from ethylacetate/acetone, to yield 0.5g of the title compound.

$C_{22}H_{30}N_2O_2 \cdot HCl$
M.W. = 390.92
$[\alpha]^{20}D = -35.9°$ (C=1 in MeOH)

EXAMPLE 7

(2S)-1-[1-oxo-3,4-dihydro-(2H)-1-benzothiin-6-yl]acetyl-2-(pyrrolidin-1-yl)methyl-piperidine hydrochloride 0.395g (1mmoles) of (2S)-1-[-3,4-dihydro-(2H)-1-benzothiin-6-yl]acetyl-2-(pyrrolidin-1-yl)methyl piperidine hydrochloride, prepared as described in Example 1 from [3,4-dihydro-(2H)-1-benzothiin6-yl]acetic acid (see DE-A-2106045) and (2S)-2-pyrrolidin-1-yl)methyl-piperidine, dissolved in 0.5ml of 95% MeOH were added dropwise at 0° C. to 2.1ml of a 0.5M solution of NaIO₄ in H₂O.

After 3 hours at room temperature the solution was evaporated in vacuo to dryness, taken up with AcOEt and an HCl saturated Et₂O solution to yield 0.3g of the title compound.

$C_{21}H_{30}N_2O_2S \cdot HCl$
M.W. = 410.995

The Examples are summarised in table 1.

TABLE 1

General Structure

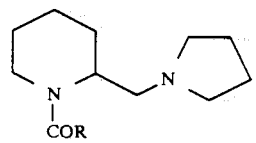

| Example No. | R | Molecular Formula | $[\alpha]_D$ C = 1 |
|---|---|---|---|
| 1 | 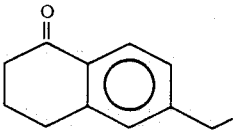 | $C_{22}H_{30}N_2O_2 \cdot HCl$ | |
| 2 | " | $C_{22}H_{30}N_2O_2 \cdot HCl$ | −49.2° (MeOH) |
| 3 | 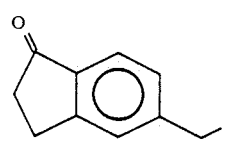 | $C_{21}H_{28}N_2O_2$ | |

TABLE 1-continued

General Structure

| Example No. | R | Molecular Formula | $[\alpha]_D$ C = 1 |
|---|---|---|---|
| 4 | (2-Me, 4-Et benzoyl) | $C_{23}H_{30}N_2O_2$ .HCl .H$_2$O | $-57.6°$ (EtOH) |
| 5 | (6-Et-2-naphthoyl) | $C_{23}H_{32}N_2O_2$ | |
| 6 | (7-Et-1-oxo-tetralin-yl) | $C_{22}H_{30}N_2O_2$.HCl | $-35.0°$ (MeOH) |
| 7 | (ethyl-phenyl-sulfonyl) | $C_{21}H_{30}N_2O_2S$.HCl | |

The pharmacological activity of the compounds of this invention is illustrated by various in vitro and in vivo models, using the following test procedures, in which the mousetail flick test demonstrates analgesic activity. The results are summarised in Table 2.

PHARMACOLOGICAL TESTS (A) P-phenylquinone-induced abdominal writing test in mice The methodology employed is based on that described by Sigmund et al, Proc. Soc. Exptl. Biol. 95, 729/1957, modified by Milne and Twomey, Agents and Actions, 10, 31/1980.

Male Charles River mice (Swiss Strain), 25-36g body weight, were used. Animals were allowed food and water ad libitum and were randomized into groups of 10 prior to experimentation. Test compounds were dissolved in either distilled water or distilled water plus 0.1 M AMS, and administered by the subcutaneous route in a final volume of 10 ml/Kg. Control animals received 10 ml/Kg of the appropriate vehicle alone. Following a pretreatment period of 20 min., mice were injected intraperitoneally with p-phenylquinone, 2 mg/Kg at 37° C. in a final volume of 10 mg/Kg. Next, the mice were placed, in groups of 3, in a compartmented perspex box maintained at room temperature and were observed for a period of 8 min. During this period the number of abdominal writhing responses per animal were recorded where writhing consists of an intermittent contraction of the abdomen associated with hind leg extension.

The degree of antinociceptive protection afforded by the test compound was determined as the mean number of writhing responses observed in the treated group (T) expressed as a percentage of the mean number of writhing responses in the control group (C) according to the following formula:

[1-(T/C)] × 100% = % graded protection (B) Tail-flick test in mice

The methodology employed is based on that described by D'Amour and Smith, J. Pharmacol. Exp. Ther. 72. 74/1941.

Male Charles River mice (Swiss Strain), 22-34g body weight were used. Animals were allowed food and water ad libitum and were randomized into groups of 10 prior to experimentation. Before administration of the test compound, the reaction time of each animal was determined by focusing a beam of light onto the tail, eliciting a reflex withdrawal after a certain latency; only mice exhibiting a latency between 3-8 sec. were used subsequently in the evaluation of drug effects.

Test compounds were dissolved in either distilled water or distilled water plus 0.1 M AMS and administered by the subcutaneous route in a final volume of 10 ml/Kg. Control animals received 10 ml/kg of the appropriate vehicle alone. Following a pretreatment period of 30 min., the mice were again placed under the heat source and the reaction tine re-determined.

Percentage quantal protection was determined as the number of mice in which the reaction time was doubled compared to pretreatment values, expressed as a percentage of the total number of mice in the group.

RECEPTOR AFFINITY STUDY

Tissue Preparation

Radio receptor binding to μ and K sites is performed on fresh guinea pig brain homogenate prepared according to Kosterlitz. (1981).

Whole brain without cerebellum is homogenized in 50 mM, Tris-buffer (pH 7.4 at 0° C.) and centrifuged at 49,000×g×10 min.

The pellet is then resuspended in the same buffer, incubated at 37° C. for 45 min. and centrifuged again.

1.9ml of the final homogenate (1:100 in Tris-pH 7.4, 0° C.) is used for the binding assay.

Binding to μ sites (Magnan J., 1982)

$^3$H [D-Ala$^2$, MePhe$^4$, Gly-ol$^5$] Enkephalin ($^3$H-DAGO), an enkephalin analogue that binds selectively to μ receptor, is added to the biological substrate and incubated at 25° C. for 40 min., filtered through Whatman GF-C and washed with ice-cold Tris-buffer.

The filters are then dryed, solubilized in Filtercount and the radioactivity monitored. Non specific binding is determined in the presence of 10$^{-6}$M Naloxone.

Binding to K sites (Magnan J., 1982)

The binding to the K-sites is performed using $^3$H-Ethyl Ketocyclazocine, a non-selective benzomorphan compound which binds to μ, δ and K-sites, in the presence of 100nM of unlabelled DAGO and 100nM of the enkephalin analogue [DAla$^2$-DLeu$^5$]Enkephalin (DADLE), to prevent μ and δ binding respectively.

Final homogenate with solutions of the cold ligand and of the labelled ligand is incubated for 40 min. at 25° C., filtered through Whatman GF/C glass filter discs and washed.

The radioactivity bound to the filters is counted by liquid scintillation spectrophotometry.

The non-specific binding is determined in the presence of 500nM of the benzomorphan non-selective compound Mr 2266.

Binding to δ sites (Magnan J., 1982)

For binding experiments, $^3$H-DADLE, which binds to μ and δ sites, is used in the presence of 30nm of unlabelled DAGO to prevent μ binding. A concentration of radioligand near KD is used in the binding assays evaluating compounds of the invention. Non-specific binding is determined by addition of Mr 2266 2.5μM.

The tubes are incubated for 40 min at 25° C. and bound ligand is separated from free by filtration through Whatman GF/G filters. The level of bound radioactivity on the filters is measured by liquid scintillation after solubilization in Filtercount.

The equilibrium dissociation constant (KD) and the maximum binding capacity (Bmax) are determined from the analysis of saturation curves, while the inhibition constant (Ki) is determined from the analysis of competition experiments (Hill 1910; Scatchard 1949; Cheng and Prusoff 1973; Gillan et al. 1980) Published references are summarised as follows:

| | |
|---|---|
| Hill, A. V. (1910) | J. Physiol. 40, IV–VIII (1910) |
| Scatchard G. (1949) | Ann. N.Y. Acad. Sci., 51, 660–674 |
| Cheng and Prusoff W. H. (1973) | Biochem. Pharmac. 22, 3099–3102 |
| Gillan M. G. C., Kosterlitz H. W. and Paterson S. Y. (1980) | Br. J. Pharmac. 70, 481–490 |
| Kotsterliz H. W., Paterson S. Y. and Robson L. E. (1981) | Br. J. Pharmac. 73, 939–949 |
| Magnan J., Paterson S. Y., Tavani A., and Kosterlits H. W. (1982) | Arch. Pharmacol. 319, 197–205 |

TABLE 2
PHARMACOLOGICAL DATA

| Example No. | MOUSE TAIL-FLICK Dose mg/kg | MOUSE TAIL-FLICK % Analgesia | MOUSE WRITHING ED$_{50}$ (mg/kg) | OPIATE RECEPTOR BINDING Ki = nM Kappa brain | OPIATE RECEPTOR BINDING Ki = nM Kappa (spinal cord) | OPIATE RECEPTOR BINDING Ki = nM Mu (brain) |
|---|---|---|---|---|---|---|
| 1 | 0.550 | 50 | 0.235 | 81.7 | 5.24 | >1000 |
| 2 | 0.233 | 50 | 0.138 | 49.05 | 2.21 | 2984 |
| 4 | 8.6 | 80 | | | | |
| 6 | 10 | 80 | | | | |

We claim:

1. A compound, or a solvate or salt thereof, of the formula (I):

$$\begin{array}{c}(CH_2)_p\\ \diagdown\\ N\quad CHR_3NR_1R_2\\ |\\ CO.R\end{array}$$

in which:
R$_1$ and R$_2$ are independently hydrogen, alkyl of 1 to 6 carbon atoms, alkenyl of 2 to 6 carbon atoms, cycloalkyl of 3 to 6 carbon atoms or cycloalkylalkyl of 4 to 12 carbon atoms, or together form a branched or linear polymethylene of 2–8 carbon atoms or alkenylene of 2–6 carbon atoms wherein one —CH$_2$— moiety thereof may be replaced by oxygen or sulphur, provided that R$_1$ and R$_2$ are not simultaneously hydrogen;
R$_3$ is hydrogen, alkyl of 1 to 6 carbon atoms, or phenyl;
p is 1, 2, 3, or 4 and
R is a group of the formula $$-CH_2-\underset{}{\bigcirc}\overset{O}{\underset{\|}{C}}(CH_2)_3$$

in which the —CH$_2$— is in the meta —or para-position with respect to —C— and one or more of the ring (—CH$_2$) groups is unsubstituted or substituted by alkyl of 1 to 6 carbon atoms.

2. A compound according to claim 1, in which each of R$_1$ and R$_2$ is methyl, ethyl, propyl, butyl, pentyl or hexyl.

3. A compound according to claim 1 in which R$_1$ and R$_2$ form a propylene, butylene, pentylene or hexylene group, or a —CH$_2$—CH=CH—CH$_2$—group.

4. A compound according to claim 1 in which p=2.

5. A compound according to claim 1 in which R is

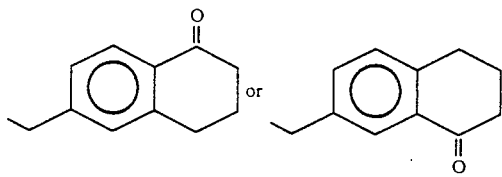

6. A compound selected from the group consisting of:
1-[1-oxo-3,4,-dihydro-(2H)-naphth-6-yl]acetyl-2-(pyrrolidin-1yl)methyl-piperidine;
(2S)-1 1-oxo-3,4,-dihydro-(2H)-naphth-6yl]acetyl-2-(pyrrolidin-1yl)methyl-piperidine;
(2S)-1-[1-oxo-2-methyl-3,4-dihydro-(2H)-naphth-6-yl]acetyl-2-(pyrrolidin-1-yl) methyl-piperidine;
(2S)-1-[1-oxo-3,4-dihydro-(2H)-naphth-7yl] acetyl-2-(pyrrolidin-1yl)methyl piperidine 7. A pharmaceutical composition useful for the treatment of pain in mammals which comprises an analgesically effective amount of a compound of the formula

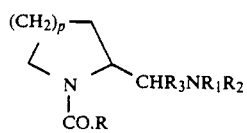

in which:
$R_1$ and $R_2$ are independently hydrogen, alkyl of 1 to 6 carbon atoms, alkenyl of 2 to 6 carbon atoms, cycloalkyl of 3 to 6 carbon atoms or cycloalkylalkyl of 4 to 12 carbon atoms, or together form a branched or linear polymethylene of 2-8 carbon atoms or alkenylene of 2-6 carbon atoms wherein one —$CH_2$— moiety thereof may be replaced by oxygen or sulphur, provided that $R_1$ and $R_2$ are not simultaneously hydrogen;
$R_3$ is hydrogen, alkyl of 1 to 6 carbon atoms, or phenyl;
p is 1, 2, 3, or 4 and
R is a group of the formula

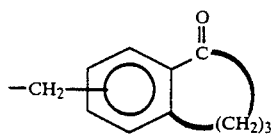

in which the —$CH_2$— is in the meta- or para-position with respect to —C— and one or more of the ring (—$CH_2$) groups is unsubstituted or substituted by alkyl of 1 to 6 carbon atoms, in combination with a pharmaceutically acceptable carrier.

8. A composition according to claim 7 in unit dosage form.

9. A pharmaceutical composition according to claim 7, in which each of $R_1$ and $R_2$ is methyl, ethyl, propyl, butyl, pentyl or hexyl.

10. A pharmaceutical composition according to claim 7, in which $R_1$ and $R_2$ together form propylene, butylene, pentylene, hexylene or —$CH_2$—CH=CH—$CH_2$—.

11. A pharmaceutical composition according to claim 7 in which p=2.

12. A pharmaceutical composition according to claim 7 in which R is

13. A pharmaceutical composition according to claim 7 wherein the compound is:
1-[1-oxo-3,4-dihydro-(2H)-naphth-6yl]acetyl-2-(pyrrolidin-1-yl)methyl-piperidine;
(2S)-1-[1-oxo-3,4-dihydro-(2H)-naphth-6yl]acetyl-2-(pyrrolidin-1yl)methyl-piperidine;
(2S)-1-[1oxo-2-methyl-3,4-dihydro-(2H)-naphth-6yl]acetyl-2-(pyrrolidin-1yl) methyl-piperidine;
(2S)-1-[1-oxo-3,4-dihydro-(2H)-naphth-7yl]acetyl-2-(pyrrolidin-1yl)methyl piperidine.

14. A method of treating pain in mammals which comprises administering to a mammal in need thereof an analgesically effective amount of a compound of the formula (I):

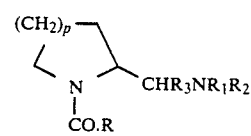

in which:
$R_1$ and $R_2$ are independently hydrogen, alkyl of 1 to 6 carbon atoms, alkenyl of 2 to 6 carbon atoms, cycloalkyl of 3 to 6 carbon atoms or cycloalkylalkyl of 4 to 12 carbon atoms, or together form a branched or linear polymethylene of 2-8 carbon atoms or alkenylene of 2-6 carbon atoms wherein one —$CH_2$— moiety thereof may be replaced by oxygen or sulphur, provided that $R_1$ and $R_2$ are not simultaneously hydrogen;
$R_3$ is hydrogen, alkyl of 1 to 6 carbon atoms, or phenyl;
p is 1, 2, 3, or 4 and
R is a group of the formula

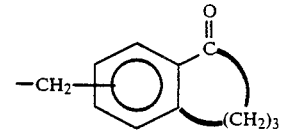

in which the —$CH_2$— is in the meta- or para-position with respect to —C— and one or more of the ring (—$CH_2$) groups is unsubstituted or substituted by alkyl of 1 to 6 carbon atoms, in combination with a pharmaceutically acceptable carrier.

15. The method according to claim 14, in which each of $R_1$ and $R_2$ is methyl, ethyl, propyl, butyl, pentyl or hexyl.

16. The method according to claim 14, in which $R_1$ and $R_2$ together form propylene, butylene, pentylene, hexylene or —$CH_2$—CH=CH—$CH_2$—.

17. A method according to claim 14 in which p=2.

18. A method according to claim 14 in which R is

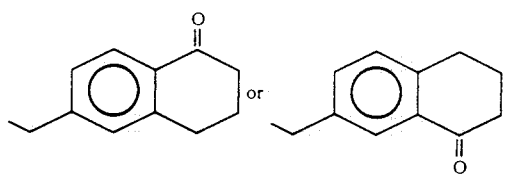
19. A method according to claim 14 wherein the compound is selected from the group consisting of:
1-[1-oxo-3,4,-dihydro-(2H)-naphth-6-yl]acetyl-2-(pyrrolidin-1methyl-piperidine;
(2S)-1-[1-oxo-3,4,-dihydro-(2H)-naphth-6-yl]acetyl-2-(pyrrolidin-1-yl)methyl-piperidine;
(2S)-1-[1-oxo-2-methyl-3,4-dihydro-(2H)-naphth-6-yl]acetyl-2-(pyrrodlidin-1-yl)methyl-piperidine:
(2S)1-[1-oxo-3,4-dihydro-(2H)-naphth-7-yl]acetyl-2-(pyrrolidin-1-yl)methyl piperdine.
* * * * *